(12) United States Patent
Plissonnier et al.

(10) Patent No.: US 7,989,056 B2
(45) Date of Patent: Aug. 2, 2011

(54) HYDROPHOBIC SURFACE COATING WITH LOW WETTING HYSTERESIS, METHOD FOR DEPOSITING SAME, MICROCOMPONENT AND USE

(75) Inventors: Marc Plissonnier, Eybens (FR); Frédéric Gaillard, Voiron (FR); Yves Fouillet, Voreppe (FR)

(73) Assignee: Commissariat A l'Energie Atomique, Paris (FR)

( * ) Notice: Subject to any disclaimer, the term of this patent is extended or adjusted under 35 U.S.C. 154(b) by 728 days.

(21) Appl. No.: 11/922,424

(22) PCT Filed: Jul. 1, 2005

(86) PCT No.: PCT/FR2005/001694
§ 371 (c)(1),
(2), (4) Date: Dec. 18, 2007

(87) PCT Pub. No.: WO2007/003720
PCT Pub. Date: Jan. 11, 2007

(65) Prior Publication Data
US 2009/0142564 A1    Jun. 4, 2009

(51) Int. Cl.
*B01J 19/98* (2006.01)
(52) U.S. Cl. .......... 428/220; 427/569; 106/287.13; 204/192.15
(58) Field of Classification Search .......... 428/220; 106/287; 204/192.15; 427/569
See application file for complete search history.

(56) References Cited

U.S. PATENT DOCUMENTS

| | | | |
|---|---|---|---|
| 4,243,692 A | 1/1981 | Scholze et al. | |
| 5,093,152 A * | 3/1992 | Bonet et al. | 427/575 |
| 5,718,967 A | 2/1998 | Hu et al. | |
| 6,627,532 B1 * | 9/2003 | Gaillard et al. | 438/623 |
| 6,733,868 B1 | 5/2004 | Kanbe et al. | |
| 2003/0215625 A1 * | 11/2003 | Golecki | 428/293.4 |
| 2005/0170102 A1 * | 8/2005 | Matsumoto et al. | 427/535 |
| 2005/0236694 A1 * | 10/2005 | Wu et al. | 257/632 |

FOREIGN PATENT DOCUMENTS

| | | |
|---|---|---|
| EP | 0 289 402 A1 | 11/1988 |
| EP | 1 011 298 A1 | 6/2000 |
| WO | WO 97/12966 A1 | 4/1997 |

OTHER PUBLICATIONS

F., Benitez et al., "Improvement of Hardness in Plasma Polymerized Hexamethyldisiloxane Coatings by Silica-Like Surface Modification," Thin Solid Films, vol. 377-378, pp. 109-114, Dec. 1, 2000.
D., Hegemann et al., "Improving the Adhesion of Siloxane-Based Plasma Coating on Polymers With Defined Wetting Properties," CAPLUS, XP002326575, Abstract, Apr. 22, 2003.

* cited by examiner

*Primary Examiner* — David R. Sample
*Assistant Examiner* — Tahseen Khan
(74) *Attorney, Agent, or Firm* — Oliff & Berridge, PLC

(57) ABSTRACT

A hydrophobic surface coating, preferably obtained by chemical vapor deposition, comprises at least an upper thin layer formed by a compound selected from the group consisting of $SiC_xO_y$:H with x comprised between 1.4 and 2 and y comprised between 0.8 and 1.4 and $SiC_{x'}N_{y'}$:H with x' comprised between 1.2 and 1.4 and y' comprised between 0.6 and 0.8, so as to obtain a free surface with a low wetting hysteresis. Such a hydrophobic surface coating can be arranged on the free surface of a microcomponent comprising at least one substrate provided with, an electrode array and particularly suitable for moving drops of liquid by electrowetting on dielectric.

26 Claims, 6 Drawing Sheets

HYDROPHOBIC SURFACE COATING WITH LOW WETTING HYSTERESIS, METHOD FOR DEPOSITING SAME, MICROCOMPONENT AND USE

BACKGROUND OF THE INVENTION

The invention relates to a hydrophobic surface coating.

The invention also relates to a method for depositing a such surface coating, a microcomponent comprising at least a substrate provided with an electrode array and having a surface designed to receive a drop of liquid, and the use of one such microcomponent.

STATE OF THE ART

In a large number of fields where analysis of aqueous solutions is involved, such as the field of chemical, biological, biochemical and environmental analysis, the medical field or quality control, the development of microtechnologies has enabled microcomponents forming labs-on-chip to be achieved. Such labs-on-chip enable to miniaturize the volumes of liquid to be analyzed, while at the same time increasing the speed and sensitivity of the measurements. These microcomponents generally comprise channels or cavities which can generate interactions between the solutes and the walls of the channels or of the cavities as well as reactive entity absorption phenomena limiting the reaction efficiencies or forming sources of contamination.

It has therefore been proposed to fabricate microcomponents in which the channels or walls are eliminated, thereby enabling each drop of liquid placed on a free surface of a microcomponent to form an independent microreactor and to move freely from one point of the free surface to another. One of the methods of movement and/or handling of the drops makes use for example of the electrowetting-on-dielectric (EWOD) principle.

The electrowetting-on-dielectric principle consists in depositing a drop on a substrate comprising a first electrode array and coated with a hydrophobic insulating coating. A second electrode array is arranged facing the first array, above the drop, so as to apply a voltage locally between two electrodes of the first and second arrays. The surface of the coating zone where the voltage is applied moreover forms a capacitance, it charges and attracts the drop creating a force which causes movement or spreading of the drop. It is then possible, step by step, to move liquids and to mix them. The electrowetting principle is also used in microcomponents comprising channels or cavities, to facilitate for example movement of the liquid inside the channel.

However, the electrowetting principle requires the free surface on which the drop is placed to be very hydrophobic. The hydrophobicity of a surface is defined by the contact angle between the surface and the meniscus of a drop of water located on said surface. The greater the difference between the contact angle in the initial state, i.e. before the movement or spreading force is applied, and that obtained when the force is applied, the greater the movement. Furthermore, the greater the contact angle in the initial state, the lower the force required for movement or spreading of the drop. Therefore, to obtain a significant movement, an contact angle greater than or equal to 100° generally has to be obtained.

Movement, handling or deformation of a drop also has to be reversible or almost, i.e. when the force causing movement or deformation of the drop is no longer applied, the system formed by the hydrophobic surface and the drop arranged on said surface must be in a state that is as close as possible to the initial state. This reversibility essentially depends on a phenomenon called wetting hysteresis, itself dependent on the density, the uniformity of thickness, the roughness and the chemical homogeneity of the surface. The wetting hysteresis of a surface in fact determines the state of the system after the spreading or movement force has been applied, which makes it possible to determine whether a second spreading or movement can be performed. However, as the hydrophobicity and wetting hysteresis parameters are related, the more hydrophobic a surface is, the lesser the effect the wetting hysteresis has on movement of the drop.

The wetting hysteresis of a surface or wetting-dewetting hysteresis in fact corresponds to a refusal to wet a dry surface, when the drop slides on said surface, this phenomenon then manifesting itself by an increase of the contact angle on the side where the drop advances, also called advancing angle $\theta_a$. Likewise, a previously wetted surface tends to retain the drop, which generates a smaller contact angle on the side where the drop recedes, also called receding angle $\theta_r$. For illustration purposes, the advancing angle $\theta_a$ and the receding angle $\theta_r$ are represented in FIG. 1 where an inclined substrate 1 comprises a hydrophobic surface coating 2 whereon a drop 3 is disposed. The wetting hysteresis of the surface coating 2 is thereby determined by measuring the difference between the maximum advancing angle $\theta_{a\,max}$ and the minimum receding angle $\theta_{r\,min}$. The greater this difference, the greater the wetting hysteresis of the surface coating and the more difficulty the drop of water has to move. Generally speaking, in the electrowetting-on-dielectric field, it is desirable to obtain a hydrophobic surface coating having a wetting hysteresis less than or equal to 15°.

The hydrophobic coatings used to form the free surface of microcomponents suitable for electrowetting on dielectric generally comprise liquid fluorinated polymer such as Teflon® marketed by the DuPont Company. However, although Teflon® is very hydrophobic, with an contact angle equal to 110°, its relative dielectric constant value is about 2 and it presents a low breakdown coefficient. To remedy a low breakdown coefficient, the Teflon® surface coating is generally thick and the voltage required to move a drop is high. Moreover, a thin dielectric layer is arranged between the Teflon® coating and the surface of the microcomponent to compensate the low dielectric constant of Teflon®. Finally, Teflon® presents the drawback of generally being spin coated. This technique is however only applicable to perfectly flat surfaces, which limits the use of a Teflon® coating in the electrowetting-on-dielectric field.

It has been proposed to replace Teflon® by Parylene as the latter can be deposited by vacuum evaporation. This technique in fact enables a coating having a relatively uniform thickness to be obtained whatever the geometry of the surface on which it is applied. In addition, Parylene has a satisfactory dielectric constant and a good breakdown strength. This compound is not however sufficiently hydrophobic, the contact angle being equal to 90°, and it comprises a too high wetting hysteresis to enable it to be used in a device using the electrowetting-on-dielectric phenomenon.

OBJECT OF THE INVENTION

One object of the invention is to obtain a hydrophobic surface coating remedying the above-mentioned shortcomings and more particularly having a relatively low wetting hysteresis, preferably less than 15°, while keeping a good hydrophobicity and a high relative dielectric constant.

According to the invention, this object is achieved by the fact that the hydrophobic surface coating comprises at least a top thin layer formed by a compound chosen among $SiC_xO_y$:H with x comprised between 1.4 and 2 and y comprised between 0.8 and 1.4 and $SiC_{x'}N_{y'}$:H with x' comprised between 1.2 and 1.4 and y' comprised between 0.6 and 0.8, so as to obtain a free surface with a low wetting hysteresis.

According to a development of the invention, the top thin layer has a thickness less than or equal to 1 micrometer.

According to a preferred embodiment, the surface coating comprises a dielectric bottom thin layer.

According to another feature of the invention, the bottom thin layer has a relative dielectric constant greater than or equal to 2.

It is a further object of the invention to provide a method for depositing a such surface coating on a face of a microcomponent, a method that is easy to implement and enables a surface coating having a constant thickness to be obtained whatever the geometry of the microcomponent.

According to the invention, this object is achieved by the fact that the method for depositing consists at least in performing chemical vapor deposition on the face of said microcomponent to form a top thin layer consisting of a compound selected among $SiC_xO_y$:H with x comprised between 1.4 and 2 and y comprised between 0.8 and 1.4 and $SiC_{x'}N_{y'}$:H with x' comprised between 1.2 and 1.4 and y' comprised between 0.6 and 0.8, chemical vapor deposition being performed by means of a precursor selected from organosilanes.

According to a development of the invention, the chemical vapor deposition is plasma enhanced chemical vapor deposition preferably performed in pulsed mode.

It is a further object of the invention to provide a microcomponent comprising at least a substrate provided with an electrode array and having a surface which is designed to receive at least one drop of liquid able to move and/or deform easily and quickly on the surface of the microcomponent.

According to the invention, this object is achieved by the fact that the microcomponent comprises a surface coating according to the invention and arranged on the face of the microcomponent in such a way that the free surface of the coating receives the drop.

Such a microcomponent can then be used by successively applying a voltage to the different electrodes so as to move the drop arranged on the free surface of the coating.

BRIEF DESCRIPTION OF THE DRAWINGS

Other advantages and features will become more clearly apparent from the following description of particular embodiments of the invention given for non-restrictive example purposes only and represented in the accompanying drawings, in which.

DESCRIPTION OF PARTICULAR EMBODIMENTS

Figure 1:
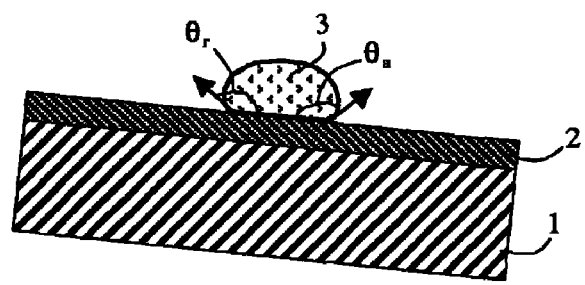
FIG. 1 represents, in cross-section, an inclined substrate comprising a surface coating whereon a drop is disposed.

According to the invention, a hydrophobic surface coating comprises at least one upper layer consisting of a compound selected among $SiC_xO_y$:H and $SiC_{x'}N_{y'}$:H, with x comprised between 1.4 and 2 and y comprised between 0.8 and 1.4 and with x' comprised between 1.2 and 1.4 and y' comprised between 0.6 and 0.8. The upper thin layer preferably has a thickness less than or equal to 1 micrometer.

What is meant by $SiC_xO_y$:H is a compound selected among carbon-doped amorphous hydrogenated silicon oxides, the atomic proportion of carbon compared with the atomic proportion of oxygen corresponding to the ratio x/y.

What is meant by $SiC_{x'}N_{y'}$:H is a compound selected among carbon-doped amorphous hydrogenated silicon nitrides, the atomic proportion of carbon compared with the atomic proportion of nitrogen corresponding to the ratio x'/y'.

Such a choice of compounds able to form the upper layer of the hydrophobic surface coating is determined by the nature of the chemical bonds present in the compounds. $SiC_xO_y$:H and $SiC_{x'}N_{y'}$:H do in fact each comprise chemical bonds of Si—$CH_3$ type, i.e. the chemical bonds present between a silicon atom and a —$CH_3$ group. Si—$CH_3$ bonds do however make the free surface of the upper layer particularly hydrophobic and give it a low wetting hysteresis. Moreover, the oxygen atom or the nitrogen atom present in the compound gives the thin layer a high relative dielectric constant, preferably greater than or equal to 2, and a good breakdown strength. In addition, the compounds selected from $SiC_xO_y$:H and $SiC_{x'}N_{y'}$:H are biocompatible, the thin layers formed by such compounds then being suitable for microcomponents used in the medical or biological field.

In a particular embodiment, the surface coating is deposited on the surface of a microcomponent, and forms at least the upper thin layer on the surface of the microcomponent. Formation of the upper thin layer is achieved by chemical vapor deposition by means of a precursor selected from organosilanes. The chemical vapor deposition is preferably plasma enhanced chemical vapor deposition, also called PECVD, more particularly in pulsed mode. Performing PECVD in pulsed mode in fact enables the roughness of a surface to be modified and the wetting hysteresis of the surface to therefore be significantly reduced. For an upper thin layer made of $SiC_xO_y$:H, the organosilane precursor is for example octamethylcyclotetrasiloxane (OMCTS) and it is mixed with helium. For an upper thin layer made of $SiC_{x'}N_{y'}$:H, the organosilane precursor is for example tetramethylsilane (TMS) mixed with nitrogen.

Thus for example, the upper thin layer is deposited on the surface of a microcomponent arranged in a vacuum deposition device. The vacuum deposition device is for example a chamber for performing chemical vapor deposition enhanced by a plasma excited by a capacitive discharge at 13.56 MHz. A low-frequency or radiofrequency generator then enables a plasma discharge to be performed close to the microcomponent, and the precursor, mixed with helium or nitrogen, is injected into the chamber at reduced pressure.

Achieving such a surface coating in particular enables technologies compatible with microelectronics techniques to be used, depositions of coatings to be made on very large surfaces and the fabrication steps of a microcomponent suitable for electrowetting on dielectrics to be reduced. Furthermore, chemical vapor deposition enables the compound of the upper thin layer to be in a particular chemical structure, by forming in particular Si—$CH_3$ type chemical bonds. Moreover, the choice of the compounds forming the upper thin layer enables a deposition method to be used that is easy to implement and enables a surface coating to be achieved having a constant thickness whatever the geometry of the microcomponent, unlike other compounds used for liquid displacement such as Teflon®. This is particularly suitable for microcomponents comprising a cavity or a channel with a depth having a thickness of several hundred micrometers.

Figure 4:
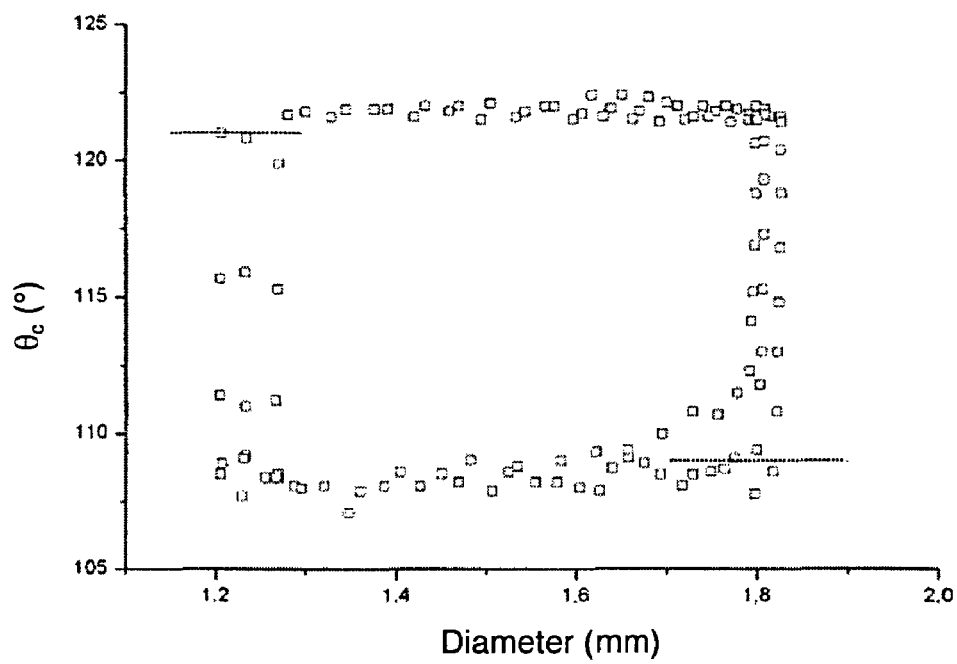
FIGS. 4 and 5 graphically represent the wetting hystereses of two surface coatings compound of Teflon®, respectively deposited by spin coating and by PECVD.
Figure 5:
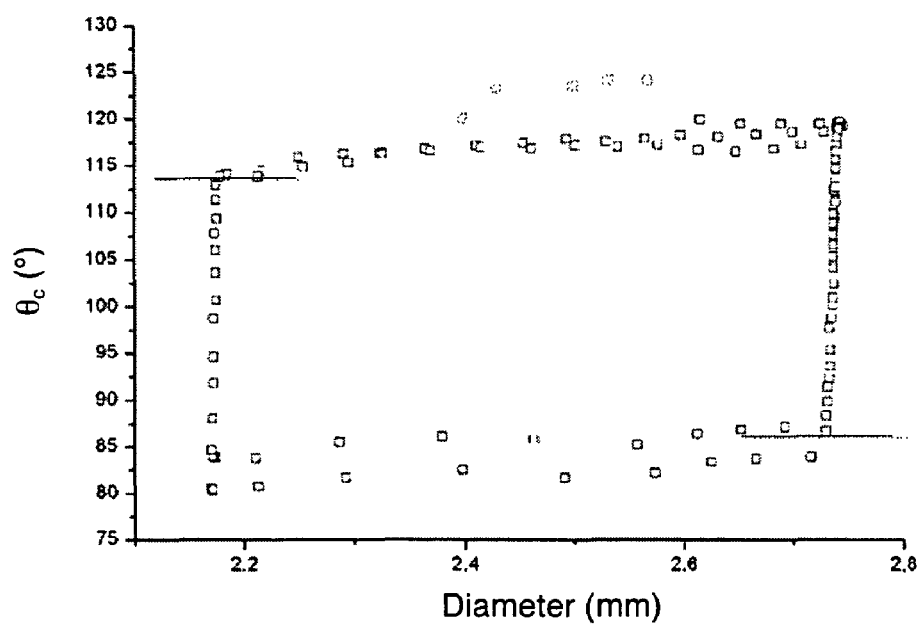
Figure 6:
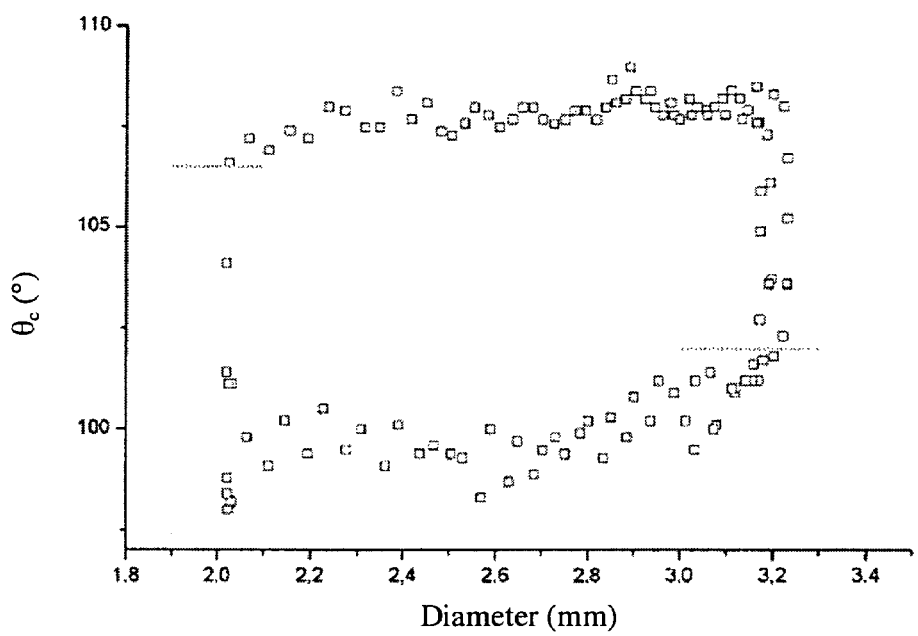
FIGS. 6 and 7 graphically represent the wetting hystereses of two surface coatings compound of $SiC_{1.6}O_{1.2}$:H, respectively in conformation A and conformation B and deposited by PECVD.
Figure 7:
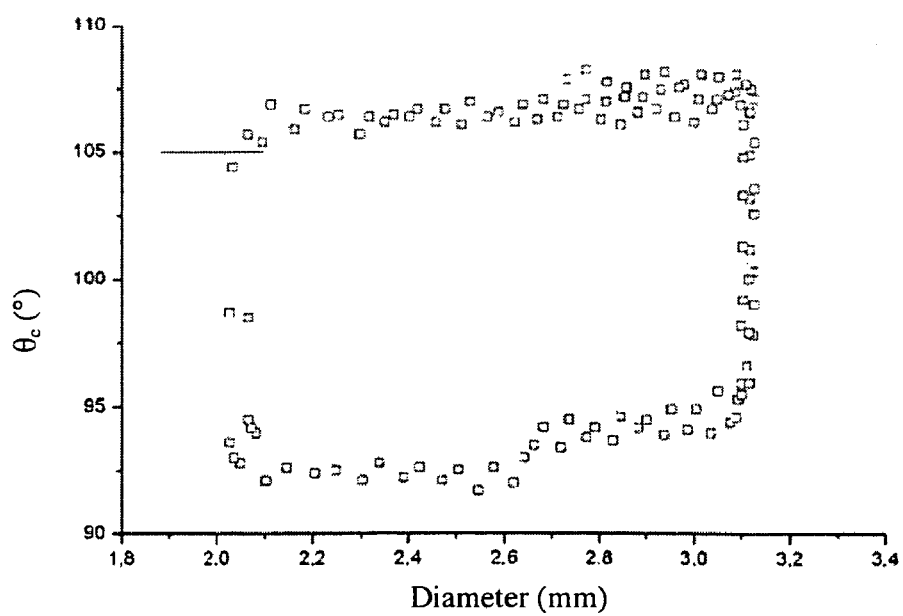

For comparison purposes, the wetting angle and wetting hysteresis were measured (FIGS. 4 to 7) for surface coatings respectively formed by:
a thin layer of Teflon® deposited by spin coating (FIG. 4),
a thin layer of Teflon® deposited by PECVD (FIG. 5),
a thin layer of $SiC_{1.6}O_{1.2}$:H deposited by PECVD by means of a cyclic organosilane precursor enabling a conformation or a chemical structure A of the $SiC_{1.6}O_{1.2}$:H compound to be obtained, noted $SiC_{1.6}O_{1.2}$:H (A) (FIG. 6)
and a thin layer of $SiC_{1.6}O_{1.2}$:H deposited by PECVD by means of a cyclic organosilane precursor enabling a conformation or a chemical structure B of the $SiC_{1.6}O_{1.2}$:H compound to be obtained, noted $SiC_{1.6}O_{1.2}$:H (B) and different from conformation A (FIG. 7).

For the $SiC_{1.6}O_{1.2}$:H (A) compound, deposition is for example performed by injecting a mixture of OMCTS and helium into the deposition chamber. The mixture is made beforehand in a bottle heated to 60° C. by means of a helium bubbling system with a flow rate of about 0.2 liters par minute. The OMCTS/He mixture is then diluted in helium with a flow rate of 0.632 $cm^3$/min to be injected into the chamber. The power applied to the electrode generating the plasma is 0.02 W/$cm^2$, the distance between the electrodes is 30 mm, and the pressure inside the chamber is maintained at 0.2 mbar during deposition of the thin layer.

For the $SiC_{1.6}O_{1.2}$:H (B) compound, deposition is for example performed by injecting a mixture of OMCTS and helium into the deposition chamber. The mixture is made beforehand in a bottle heated to 60° C. by means of a helium bubbling system with a flow rate of about 0.4 liters per minute. The OMCTS/He mixture is then diluted in helium with a flow rate of 0.273 $cm^3$/min to be injected into the chamber. The power applied to the electrode generating the plasma is 0.81 W/$cm^2$, the distance between the electrodes is 15 mm and the pressure inside the chamber is maintained at 0.2 mbar during deposition of the thin layer.

The thin layers of $SiC_{1.6}O_{1.2}$:H (A) and $SiC_{1.6}O_{1.2}$:H (B) have a thickness of 1 micrometer.

Figure 2:
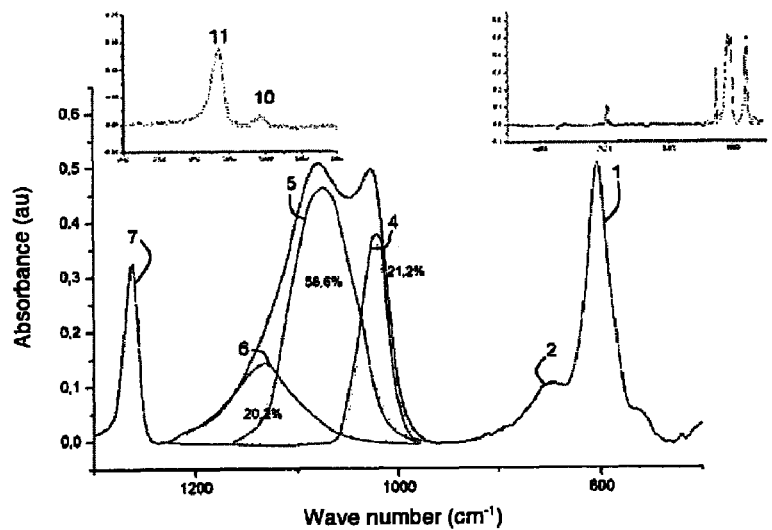
FIGS. 2 and 3 represent the infrared spectra of two $SiC_{1.6}O_{1.2}$:H compounds respectively in conformation A and conformation B.
Figure 3:
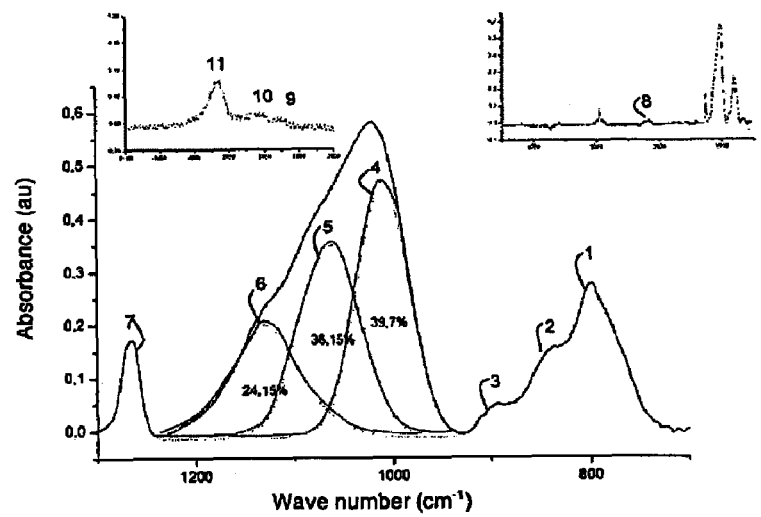

Conformations A and B of $SiC_{1.6}O_{1.2}$:H are determined by infrared spectroscopy (FTIR) respectively illustrated in FIGS. 2 and 3. Analysis of the infrared spectra provides qualitative and semi-quantitative information on the nature of the chemical bonds present in the $SiC_{1.6}O_{1.2}$:H (A) and $SiC_{1.6}O_{1.2}$:H (B) compounds. Each IR spectrum absorption peak in fact occurs at a wave number corresponding to a vibration mode proper to a particular chemical bond. Table 1 below indicates the corresponding vibration mode for each absorption peak of FIGS. 2 and 3.

TABLE 1

| Absorption peak reference | Wave number ($cm^{-1}$) | Vibration mode - Corresponding bond |
|---|---|---|
| 1 | 800 | $\partial_r\, CH_3$ in $Si(CH_3)_2$ |
| 2 | 840 | $\partial_r\, CH_3$ in $Si(CH_3)_3$ |
| 3 | 890 | $\upsilon$ SiH |

TABLE 1-continued

| Absorption peak reference | Wave number ($cm^{-1}$) | Vibration mode - Corresponding bond |
|---|---|---|
| 4 | 1020 | $\upsilon_a$ linear SiOSi |
| 5 | 1080 | $\upsilon$ cyclic SiOSi |
| 6 | 1130 | $\upsilon$ SiOC in $SiOCH_3$ |
| 7 | 1250-1270 | $\partial_s\, CH_3$ in $Si(CH_3)_{3/2/1}$ |
| 8 | 2165 | $\upsilon_s$ SiH |
| 9 | 2875 | $\upsilon_s$ CH in $CH_2$ |
| 10 | 2905 | $\upsilon_s$ CH in $CH_3$ |
| 11 | 2960 | $\upsilon_s$ CH in $CH_3$ |

In FIG. 2, it can be observed that the infrared spectrum of the $SiC_{1.6}O_{1.2}$:H (A) compound comprises two peaks 1 and 7 corresponding to the —Si—$CH_3$ bond contained in the —Si($CH_3$)$_2$ and —Si($CH_3$)$_3$ groups. Furthermore, it comprises peaks 4, 5 and 6 corresponding to the —Si—O— chemical bond. According to table 1, 58.6% of the —Si—O— chemical bonds are present in cyclic —Si—O—Si— form (peak 5) corresponding to the cyclic structure of the precursor used to perform chemical vapor deposition, 21.2% of the —Si—O— chemical bonds are present in linear —Si—O—Si form corresponding to opening of the precursor cycles (peak 4) and 20.2% of the —Si—O— chemical bonds are present in the form of —Si—O—C— of the Si—O—$CH_3$ group (peak 6).

In FIG. 3, it can be observed that the $SiC_{1.6}O_{1.2}$:H (B) compound is much more cross-linked than the $SiC_{1.6}O_{1.2}$:H (A) compound, the number of —$CH_3$ groups (peaks 1 and 7) being smaller than in the $SiC_{1.6}O_{1.2}$:H (A) compound. Instead of the groups $CH_3$, the $SiC_{1.6}O_{1.2}$:H (B) compound contains groups of $C_xH_y$ type (peaks 2 and 3). Moreover, the structural distribution of the —Si—O— bonds is very different from that of the $SiC_{1.6}O_{1.2}$:H (A) compound. Thus, 39.7% of the —Si—O— bonds are present in linear —Si—O—Si— form (peak 4), 36.15% are in cyclic —Si—O—Si— form (peak 5) and 24.15% are in —Si—O—C— form comprised in the Si—O—$CH_3$ group. The $SiC_{1.6}O_{1.2}$:H (B) compound also contains —Si—H groups (peaks 3 and 8) which are not present in the $SiC_{1.6}O_{1.2}$:H (A) compound.

FIGS. 4 to 7 correspond to graphs measuring the contact angle ($\theta_c$ in °) versus the diameter (in mm) of a drop of water deposited on the surface of the four corresponding coatings. The angles of contact are measured by means of a camera, using a deposition system of a drop of water on the surface of the coating. For example, the system used is an automated system marketed by the Kruss Company under the name of Drop Shape Analysis system DSA 10 mk2, enabling not only the contact angle but also the wetting hysteresis to be measured by increasing and decreasing the volume of the drop. The wetting hysteresis phenomenon can then be visualized for each type of coating (Teflon, $SiC_{1.6}O_{1.2}$:H (A) and $SiC_{1.6}O_{1.2}$:H (B)) via a series of measurements and the contact angle characterizing the hydrophobicity and the wetting hysteresis can be determined for each coating. The results are set out in table 2 below.

TABLE 2

| | Contact angle ($\theta_c$ in °) | Hysteresis ($\theta_r - \theta_a$) |
|---|---|---|
| Teflon - Spin coating | 120° | 12.2° |
| Teflon - PECVD | 115° | 25° |
| $SiC_{1.6}O_{1.2}$: H (A) with a thickness of 1 μm - PECVD | 107° | 4.5 |
| $SiC_{1.6}O_{1.2}$: H (B) with a thickness of 1 μm - PECVD | 100° | 9.5 |

It can thus be observed that although the hydrophobicity of the $SiC_{1.6}O_{1.2}$:H (A) and $SiC_{1.6}O_{1.2}$:H (B) compounds is slightly lower than that of the Teflon coatings, it does however remain high, the contact angle being greater than 100°. The wetting hysteresis of the $SiC_{1.6}O_{1.2}$:H (A) and $SiC_{1.6}O_{1.2}$:H (B) compounds is on the other hand much lower than that of Teflon coatings. In addition, the $SiC_{1.6}O_{1.2}$:H (A) compound presents hydrophobicity and wetting hysteresis characteristics that are better suited to the electrowetting on dielectric field than the $SiC_{1.6}O_{1.2}$:H (B) compound.

In the same way, the wetting angle and the wetting hysteresis of a $SiC_{1.3}N_{0.7}$:H compound was measured. The wetting angle is about 92° and the hysteresis is 9°. For the $SiC_{1.3}N_{0.7}$:H compound, deposition is for example performed by injecting TMS with a flow rate of 2 cm$^3$/min, diluted with nitrogen with a flow rate of 1 l/min, into the deposition chamber. The power applied to the electrode generating the plasma is 300 W and the pressure inside the chamber is kept at 0.5 mbar during the deposition step.

Figure 8:
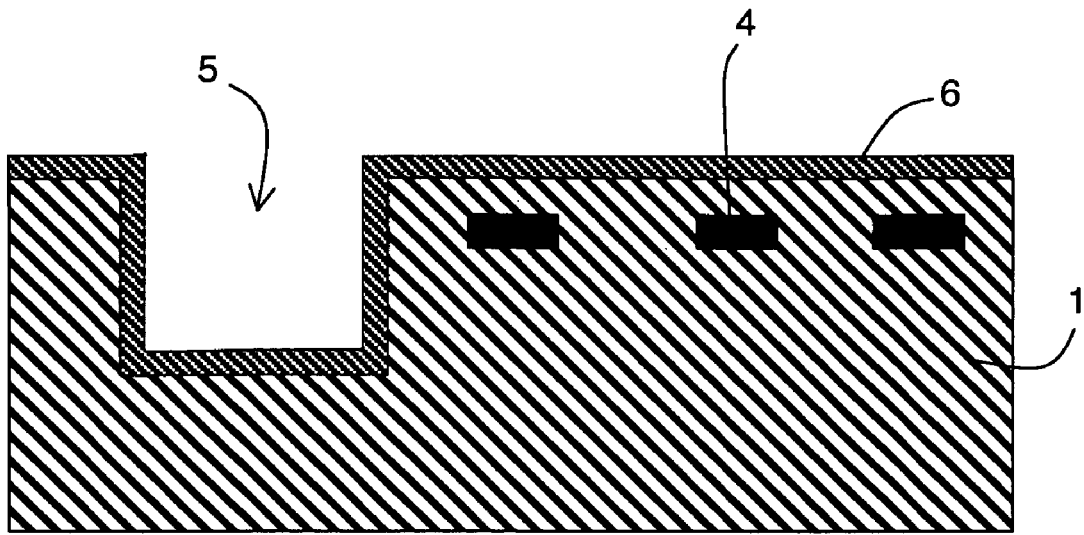
FIGS. 8 and 9 respectively represent, schematically in cross-section, first and second hydrophobic surface coatings according to the invention arranged on a microcomponent.

Such surface coatings can be arranged on the surface of a microcomponent. Thus, in a particular embodiment represented in FIG. 8, a microcomponent comprises a substrate 1 one face whereof is designed to receive at least one drop of liquid. Substrate 1 is provided with an electrode array 4 buried within the substrate and with a cavity 5. The substrate is covered by a surface coating formed by an upper thin layer 6 formed by a compound selected among $SiC_xO_y$:H and $SiC_xN_y$:H. The free surface of upper thin layer 6 is designed to receive the drop of liquid so as to move the latter, for example from the zone of the coating covering cavity 5 to another zone of the coating.

Figure 9:
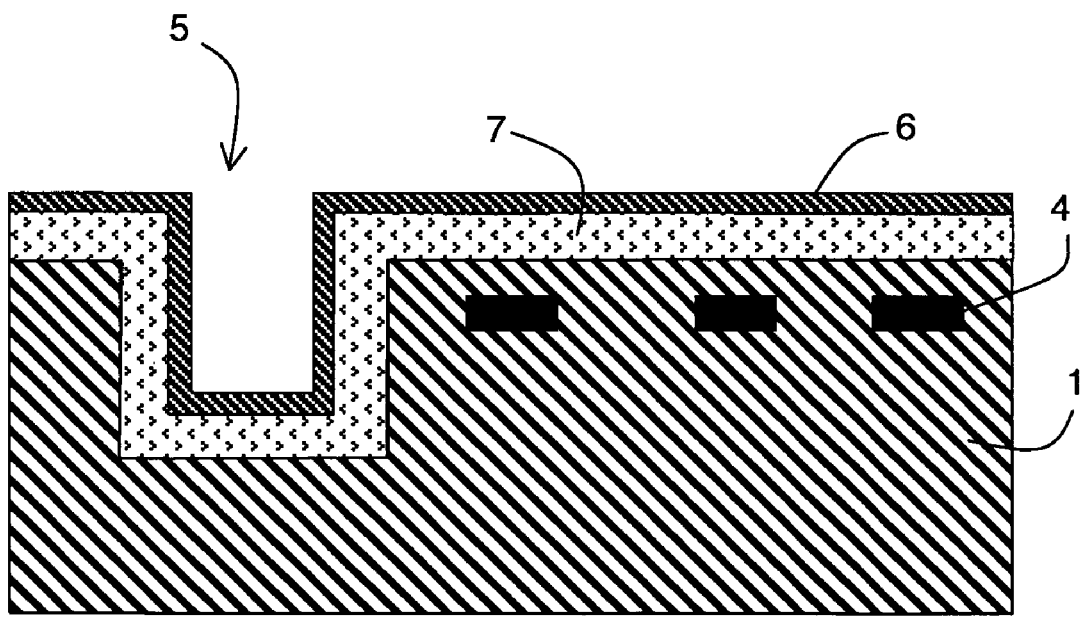

To increase the relative dielectric constant of the surface coating, a dielectric bottom thin layer 7 can be arranged under upper thin layer 6, as represented in FIG. 9. Bottom thin layer 7 is preferably deposited on the surface of the microcomponent before the deposition of the upper thin layer 6, either by plasma enhanced chemical vapor deposition (PECVD) or by magnetron sputtering. The thickness of bottom thin layer 7 is preferably less than or equal to 5 micrometers and the relative dielectric constant is preferably greater than or equal to 2. More particularly, bottom thin layer 7 is for example formed by a compound selected from the group comprising $SiO_2$, SiN, SiCN, $Ta_2O_5$, $TiO_2$, $HfO_2$, $ZrO_2$, $Al_2O_3$, $SrTiO_3$, $BaTiO_3$ and $Pb(ZrTi)O_3$. For example, PECVD of the bottom thin layer is performed under radiofrequency (RF) excitation with a precursor of $SiH_4/N_2O$ type whereas magnetron sputtering can be performed with a $Si_3N_4$ target. Such a bottom thin layer 7 strengthens the relative dielectric constant of the surface coating and increases the breakdown strength even further.

Figure 10:
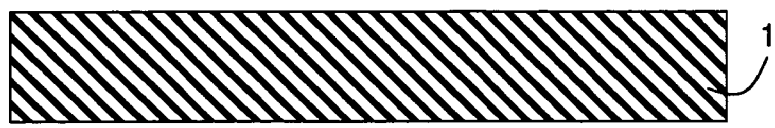
FIGS. 10 to 17 represent the different steps of fabrication of a microcomponent according to the invention.
Figure 11:
Figure 12:
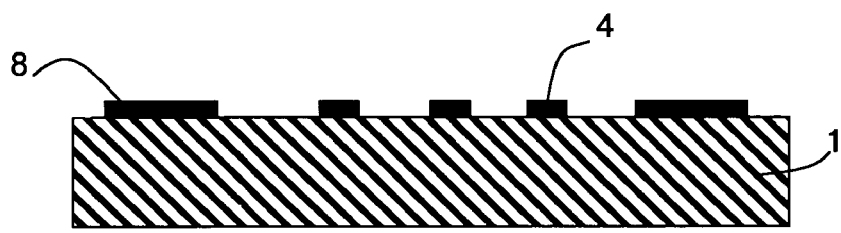
Figure 13:
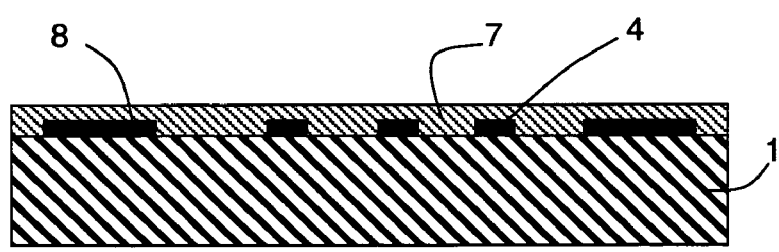

In a particular embodiment illustrated in FIGS. 10 to 16, a microcomponent is obtained from a substrate 1 as represented in FIG. 10 and comprising for example glass, silica, polycarbonate or silicon covered by an insulating layer such as silicon oxide. An electrode array 4 connected to pads 8 is then formed on the surface of substrate 1 (FIG. 12) by prior deposition of a metal thin layer 9 (FIG. 11) on the surface of substrate 1 and by then patterning the latter by photolithography. Metal thin layer 9 can for example be made of gold, aluminium, titanium, platinum or indium and tin oxide and its thickness is preferably about 0.1 μm to 2 μm.

Such microcomponents can be used to move a drop placed on the free surface of the coating by successively applying a voltage to the different electrodes.

Figure 14:
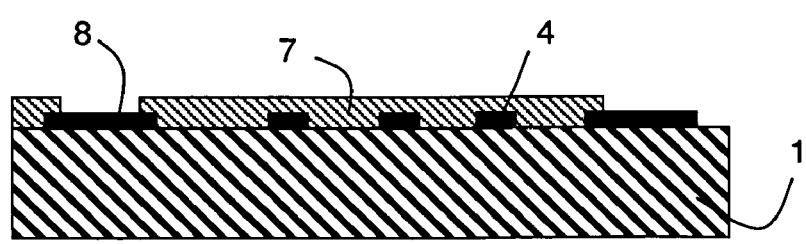
Figure 15:
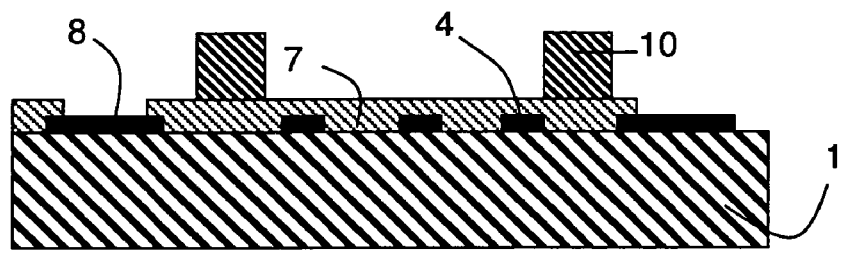

Substrate 1 provided with electrode array 4 is then covered with a bottom thin layer 7 (FIG. 13) such as a silicon oxide layer or a silicon nitride layer with a thickness of 0.1 μm to 5 μm. Bottom thin layer 7 is then locally etched at the level of pads 8 to achieve the electric contact connection (FIG. 14). Localized etching thereby enables a part only of the surface of pads 8 to be selectively released, and the rest of the free surface of the microcomponent formed by the non-released zones of pads 8, the free surface of substrate 1 and electrode array 4 remains covered by bottom thin layer 7.

A layer of photoresist such as SU8 resin is then deposited on the free surface of the microcomponent and is patterned by photolithography so as to form walls (or patterns) 10 (FIG. 15) which can for example be used as walls of a channel or of a cavity in a microfluidic component. Walls (or patterns) 10 have for example a thickness comprised between a few tens of micrometers and a few hundred micrometers.

Figure 16:
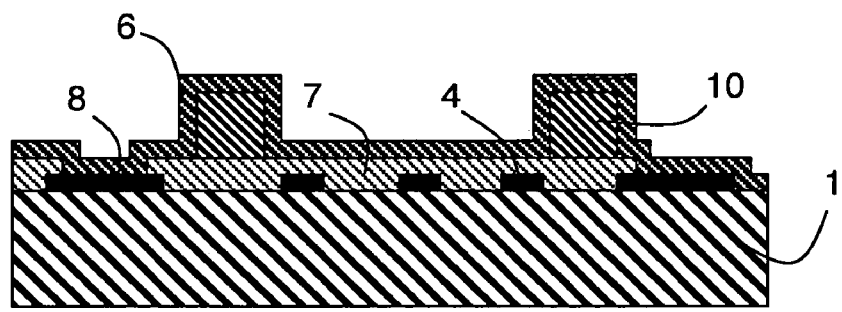

An upper thin layer 6, with a thickness comprised between 0.1 μm and 5 μm and advantageously with a thickness of 1 μm, is then deposited by PECVD on the whole of the free surface of the microcomponent (FIG. 16). It is formed by a material selected among $SiC_xO_y$:H and $SiC_xN_y$:H. Upper thin layer 6 forming the hydrophobic surface coating and having a low hysteresis therefore totally covers bottom thin layer 7 and the free part of pads 8 as well as the whole of walls 10. The substrate can then be cut so as to form individual chips that are electrically connected.

Figure 17:
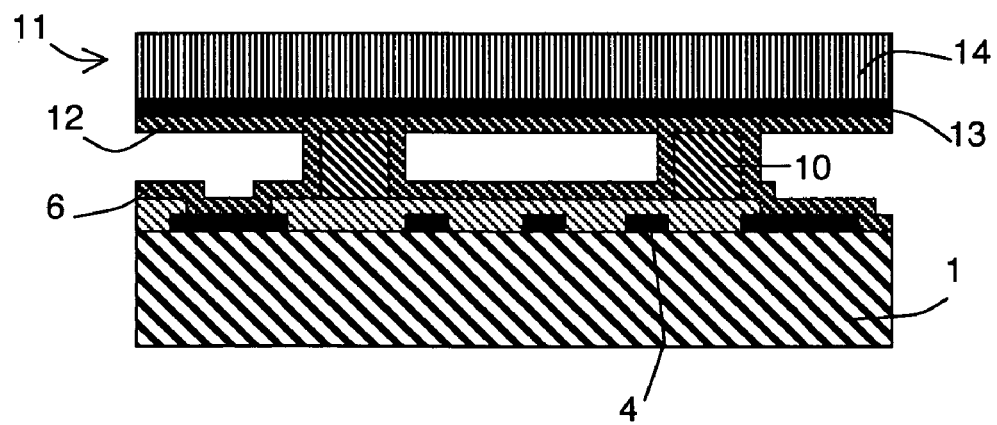

According to an alternative embodiment represented in FIG. 17, the microcomponent represented in FIG. 16 can comprise a cover 11 resting on walls 10 so as to form a channel or a cavity. Cover 11 then comprises a hydrophobic thin layer 12, a conducting layer 13 and a protective layer 14 for example made of polycarbonate, glass or silicon. Hydrophobic thin layer 12 is preferably formed by a compound selected among $SiC_xO_y$:H and $SiC_xN_y$:H and conducting layer 13 can be made of gold, aluminium, titanium, platinum or indium and tin oxide. Hydrophobic layer 12 then forms a second surface coating delineating the top wall of the channel or cavity so that the whole of the walls of the channel or cavity are hydrophobic and have a low wetting hysteresis.

According to the invention, the upper layer of a surface coating is formed by a particular selection of compounds selected from $SiC_xO_y$:H with x comprised between 1.4 and 2 and y comprised between 0.8 and 1.4 and $SiC_{x'}N_{y'}$:H with x' comprised between 1.2 and 1.4 and y' comprised between 0.6 and 0.8. This selection enables a coating to be obtained that is both hydrophobic and has a low wetting hysteresis, unlike other already known compounds. For example, Patent application EP-A-0289402 describes in general manner a protective coating made from an inorganic compound of $SiC_xN_yO_zH_t$ type, with x comprised between 0 and 5 and more particularly between 0.3 and 1, y comprised between 0 and 0.8 and more particularly between 0.5 and 0.8, z comprised between 0 and 2.5 and more particularly between 1.3 and 2 and t comprised between 0 and 1.2 and more particularly between 0.6 and 1. This inorganic compound is obtained by plasma treatment and is designed to cover a transparent polymer substrate, in particular for mechanical and antistatic protection of glass panels, screens or optic supports. The compound selected to form the upper layer of a surface coating according to the invention differs from the coating described in Patent application EP-A-0289402 in that the range of proportions of carbon, oxygen or nitrogen and hydrogen according to the invention is narrow compared with that described in Patent application EP-A-0289402. It is also far from the preferred embodiment described in Patent application EP-A-0289402. Selection of the proportions of oxygen or nitrogen and of carbon is performed not in arbitrary manner but for the purposes of obtaining a hydrophobic coating with a low wetting hysteresis.

Furthermore, in the article "Improvement of hardness in plasma polymerized hexamethyldisiloxane coatings by silica-like surface modification" (Thin Solid Films 377-378 (2000) 109-114), F. Benitez et al. study hexamethyldisiloxane-based (HMDSO) coatings polymerized by plasma (PPH-MDSO) with the object of improving protection against corrosion of the glass substrates covered with a layer of aluminium. The coatings studied are obtained from different mixtures of gases constituted by HMDSO monomer vapor and oxygen or by depositing a pure monomer and performing oxidation after deposition, by plasma treatment, and measurements of the contact angle of a film obtained under these different conditions are reported. The only case where the contact angle is greater than 100° is that where the relative oxygen pressure is zero. Moreover, analysis of the IR peaks relating to the —CH3 groups indicates that no —CH3 bond remains above 35% of oxygen in the plasma. However, F. Benitez et al. do not mention the carbon content or the specific proportions of oxygen or nitrogen and hydrogen which would have to be used to obtain a coating that is not only hydrophobic but also has a low wetting hysteresis.

The invention claimed is:

1. A hydrophobic surface coating comprising at least an uppermost thin layer formed by $SiC_xO_y$:H, with x between 1.4 and 2 and y comprised between 0.8 and 1.4, so as to obtain a free surface with a low wetting hysteresis.

2. The surface coating according to claim 1, wherein the uppermost thin layer has a thickness less than or equal to 1 micrometer.

3. The surface coating according to claim 1, wherein the surface coating comprises a dielectric bottom thin layer.

4. The surface coating according to claim 3, wherein the bottom thin layer has a thickness less than or equal to 5 micrometers.

5. The surface coating according to claim 3, wherein the bottom thin layer has a relative dielectric constant greater than or equal to 2.

6. The surface coating according to claim 3, wherein the bottom thin layer is formed by a compound selected from the group consisting of $SiO_2$, SiN, SiCN, $Ta_2O_5$, $TiO_2$, $HfO_2$, $ZrO_2$, $Al_2O_3$, $SrTiO_3$, $BaTiO_3$ and $Pb(ZrTi)O_3$.

7. A microcomponent comprising at least a substrate provided with an electrode array and having a surface on which is arranged a surface coating according to claim 1, in such a way that the free surface of the surface coating is designed to receive at least a drop of liquid.

8. The microcomponent according to claim 7, wherein a voltage is successively applied to different electrodes of the electrode array so as to move the drop arranged on the free surface of the coating.

9. A method for depositing a surface coating according to claim 1 on a surface of a microcomponent, consisting at least in performing chemical vapor deposition, by means of a precursor selected among organosilanes, on the surface of said microcomponent to form an uppermost thin layer formed by $SiC_xO_y$:H with x between 1.4 and 2 and y between 0.8 and 1.4.

10. The method for depositing according to claim 9, wherein the chemical vapor deposition is plasma enhanced chemical vapor deposition.

11. The method for depositing according to claim 10, wherein the plasma enhanced chemical vapor deposition is performed in pulsed mode.

12. The method for depositing according to claim 9, wherein the upper thin layer being made of $SiC_xO_y$:H, the precursor is formed by octamethylcyclotetrasiloxane and mixed with helium.

13. The method for depositing according to claim 9, consisting in depositing a bottom dielectric thin layer on the surface of said microcomponent, before forming the upper thin layer, by plasma enhanced chemical vapor deposition or by magnetron sputtering.

14. A hydrophobic surface coating comprising at least an uppermost thin layer formed by $SiC_{x'}N_{y'}$:H, with x' between 1.2 and 1.4 and y' comprised between 0.6 and 0.8, so as to obtain a free surface with a low wetting hysteresis.

15. The surface coating according to claim 14, wherein the uppermost thin layer has a thickness less than or equal to 1 micrometer.

16. The surface coating according to claim 14, wherein the surface coating comprises a dielectric bottom thin layer.

17. The surface coating according to claim 16, wherein the bottom thin layer has a thickness less than or equal to 5 micrometers.

18. The surface coating according to claim 16, wherein the bottom thin layer has a relative dielectric constant greater than or equal to 2.

19. The surface coating according to claim 16, wherein the bottom thin layer is formed by a compound selected from the group consisting of $SiO_2$, SiN, SiCN, $Ta_2O_5$, $TiO_2$, $HfO_2$, $ZrO_2$, $Al_2O_3$, $SrTiO_3$, $BaTiO_3$ and $Pb(ZrTi)O_3$.

20. A method for depositing a surface coating according to claim 14 on a surface of a microcomponent, consisting at least in performing chemical vapor deposition, by means of a precursor selected among organosilanes, on the surface of said microcomponent to form an upper thin layer formed by $SiC_{x'}N_{y'}$:H, with x' between 1.2 and 1.4 and y' between 0.6 and 0.8.

21. The method for depositing according to claim 20, wherein the chemical vapor deposition is plasma enhanced chemical vapor deposition.

22. The method for depositing according to claim 21, wherein the plasma enhanced chemical vapor deposition is performed in pulsed mode.

23. The method for depositing according to claim 20, wherein the upper thin layer being made of $SiC_{x'}N_{y'}$:H, the precursor is formed by tetramethylsilane and mixed with nitrogen.

24. The method for depositing according to claim 20, consisting in depositing a bottom dielectric thin layer on the surface of said microcomponent, before forming the upper thin layer, by plasma enhanced chemical vapor deposition or by magnetron sputtering.

25. A microcomponent comprising at least a substrate provided with an electrode array and having a surface on which is arranged a surface coating according to claim 1, in such a way that the free surface of the surface coating is designed to receive at least a drop of liquid.

26. The microcomponent according to claim 25, wherein a voltage is successively applied to different electrodes of the electrode array so as to move the drop arranged on the free surface of the coating.

* * * * *